United States Patent
Sugano et al.

(10) Patent No.: US 6,358,998 B1
(45) Date of Patent: Mar. 19, 2002

(54) BODY FAT-REDUCING AGENT COMPRISING DIOXABICYCLO[3.3.0] OCTANE DERIVATIVE AS ACTIVE INGREDIENT

(75) Inventors: Michihiro Sugano, Kumamoto-ken; Masanobu Sakono, Miyazaki-ken; Kazunori Koba, Nagasaki-ken; Hitoshi Okuyama, Tokyo-To; Masaaki Kasai, Nagoya; Toshio Iwata, Tokyo, all of (JP)

(73) Assignee: Rinoru Oil Mills Co., LTD, Tokyo-To (JP)

( * ) Notice: Subject to any disclaimer, the term of this patent is extended or adjusted under 35 U.S.C. 154(b) by 0 days.

(21) Appl. No.: 09/560,900

(22) Filed: Apr. 28, 2000

(30) Foreign Application Priority Data

Apr. 28, 1999 (JP) .............................. 11-122799

(51) Int. Cl.[7] .............................. A61K 31/34
(52) U.S. Cl. ...................... 514/469; 514/470
(58) Field of Search .................. 549/435; 514/469, 514/470

(56) References Cited

U.S. PATENT DOCUMENTS 5,393,774 A * 2/1995 Pieper et al. ............... 514/452

OTHER PUBLICATIONS

Chavali, SR 'Dietary alpha–linolenic acid increases TNF–a;pha and decreases IL–6, IL–10 in response to LPS: effects of sesamin on the delta–5desaturation of omega–6 and omega–3 fatty acids in mice' CA 129:27467, 1998.*

Ogawa, H 'Sesame lignans modulate cholesterol metabolism in stroke–prone spontaneously hypertensive rat' CA 124:220151, 1996.*

* cited by examiner

Primary Examiner—Amelia Owens
(74) Attorney, Agent, or Firm—Foley & Lardner

(57) ABSTRACT

There is provided an agent for reducing body fat, comprising as an active ingredient a dioxabicyclo[3.3.0]octane derivative represented by formula (I):

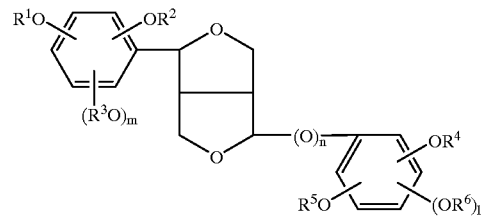

wherein $R^1$ to $R^6$ each independently represent a hydrogen atom or an alkyl group having 1 to 3 carbon atoms, provided that $R^1$ and $R^2$ and/or $R^4$ and $R^5$ combine together to form a methylene or ethylene group; and n, m, and l are each 0 or 1.

5 Claims, No Drawings

BODY FAT-REDUCING AGENT COMPRISING DIOXABICYCLO[3.3.0] OCTANE DERIVATIVE AS ACTIVE INGREDIENT

BACKGROUND OF THE INVENTION

1. Field of the Invention

The present invention relates to an agent for reducing body fat, comprising a dioxabicyclo[3.3.0]octane derivative as an active ingredient, and use of the same in the fields of food and drink products and feeds.

2. Background Art

In recent years, patients suffering from obesity have been increased also in Japan, and this is becoming a serious social problem. The Ministry of Health and Welfare has published, in November of last year, the outline of the results of the National Nutrition Survey in 1997, and has pointed out that, as compared with 10 years ago and 20 years ago, the proportion of obesity and overweight in men tends to increase, and one out of four men in twenties and one out of three men in thirties suffer from obesity or overweight. Possible factors in this include increased ingestion (hyperphagia), reduced excercise (lack of excercise), and a fluctuation in generation of body heat. Obesity causes accumulation of a large amount of body fat. This is causative of arteriosclerosis, hypertension, diabetes, and cardiac diseases, and, in some cases, leads to complications, such as angiopathy, neuropathy, and aphylaxis.

In a society these days in which health is a matter of interest, attention is drawn to the content of fat in foods, and meat having low saturated fatty acid content is preferred. Further, a great concern is shown for diet, fitness and the like for regulating body fat, particularly subcutaneous fat, visceral fat or the like, of humans.

Under these circumferences, there is a great social demand for body fat reducing agents which have excellent function and effect and are safe.

Dioxabicyclo[3.3.0]octane derivatives, particularly sesamin, are reported in an article entitled "Sesamin: A multifunctional Gift From Nature," M. Sugano and K. Akimoto, "Journal of Chinese Nutrition Society," 18, 1–11 (1993). This article describes, as possible advantages of sesamin, that sesamin interferes δ-5-desaturase, an enzyme capable of unsaturating a reaction by which dihomo-γ-linolenic acid is converted to arachidonic acid. This article further cites references discussing other possible effects of sesamin (activity to lower blood cholesterol, enhancement in detoxification of chemical materials and alcohols in the liver, protection against chemically induced breast cancer, and in vivo antioxiizing activity).

So far as the present inventors know, however, up to now, there have been no report such that dioxabicyclo[3.3.0] octane derivatives have activity to reduce body fat.

Accordingly, it is an object of the present invention to provide a novel agent for reducing body fat, which is highly stable and causes no significant side effect, and food and drink products and feeds containing the same.

SUMMARY OF THE INVENTION

The present inventors have repeated extensive and intensive studies using fat around kidney and fat around epididymis as an index of a reduction in body fat and, as a result, have found that dioxabicyclo[3.3.0]octane derivatives, which have been extracted or isolated from pepper seed, sesame meal, sesame oil or the like, or alternatively have been chemically synthesized, have activity to reduce body fat. This has led to the completion of the present invention.

Thus, the present invention provides an agent for reducing body fat, comprising a dioxabicyclo[3.3.0]octane derivative as an active ingredient, and a food or drink product and a feed having activity to reduce body fat, comprising said derivative.

DETAILED DESCRIPTION OF THE INVENTION

The dioxabicyclo[3.3.0]octane derivative to be used in the present invention is represented by formula (I):

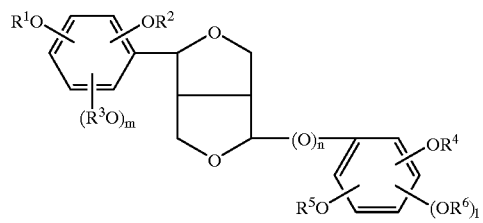

wherein $R^1$ to $R^6$ each independently represent a hydrogen atom or an alkyl group having 1 to 3 carbon atoms, provided that $R^1$ and $R^2$ and/or $R^4$ and $R^5$ may combine together to form a methylene or ethylene group; and n, m, and 1 are each 0 or 1.

Specific examples of dioxabicyclo[3.3.0]octane derivatives include sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]-octane, 2,6-bis-(3-methoxy-4-hydroxyphenyl)-3,7-dioxabicyclo[3.3.0]octane, 2-(3,4-methylenedioxyphenyl)-6-(3-methoxy-4-hydroxyphenoxy)-3,7-dioxabicyclo[3.3.0]-octane, and other compounds. Among them, sesamin, episesamin, or a mixture of sesamin with episesamin is preferred.

These compounds may also be in the form of glycoside, and optically active substances are also embraced in the present invention.

According to the present invention, the dioxabicyclo [3.3.0]octane derivatives (hereinafter referred to as "derivative of the present invention") may be used either solely or in a combination of two or more. The derivative of the present invention is not limited to a highly purified product, and may also be an extract composed mainly of one or a plurality of dioxabicyclo[3.3.0]octane derivatives described above (hereinafter referred to as the "extract composed mainly of the derivative of the present invention"). The extract composed mainly of the derivative of the present invention may be extracted from a naturally occurring product containing the derivative of the present invention by a conventional method. Naturally occurring products containing the derivative of the present invention include sesame oil, sesame meal, by-products obtained in the production process of sesame oil, sesame seed, acanthoponacis cortex, paulownia tree, bark of hakuka, long pepper, and asiasarum root. The content of the derivative of the present invention in the extract composed mainly of the derivative of the present invention is generally not less than 0.1% by weight, preferably not less than 1.0% by weight, more preferably not less than 5.0% by weight. In particular, desirably, the total content of sesamin and episesamin is not less than 0.05% by weight, preferably not less than 0.5% by weight, more preferably not less than 2.0% by weight.

When the derivative of the present invention is used as pharmaceutical preparations, the administration form may be any dosage form so far as oral administration can be conveniently carried out. The pharmaceutical preparations may be used either solely or in a combination of two or more, depending upon symptoms of patients.

These various preparations may be formulated by adding, to the basis, known adjuvants commonly used in the field of pharmaceutical preparations, such as fillers, binders, antiseptics, stabilizers, disintegrators, lubricants, and corrigents, depending upon purposes, according to a conventional method. If necessary, tonicity agents, stabilizers, antiseptics, and soothing agents may be added thereto.

External preparations, such as ointments and creams, may be formulated by a conventional method using as a base petrolatums, paraffins, fats and oils, lanolins, macrogols or the like. The dose may vary depending upon the purpose of administration and conditions of a subject, to which the preparation is to be administered, for example, sex, age, and weight. In general, however, in the case of oral administration to an adult, the dose may be properly regulated so that the total amount of the derivative of the present invention is 1 mg to 10 g, preferably 1 mg to 2 g, more preferably 1 mg to 200 mg, per day. On the other hand, in the case of parenteral administration, the dose may be properly regulated so that the total amount of the derivative of the present invention is 0.1 mg to 1 g, preferably 0.1 mg to 200 mg, more preferably 0.1 mg to 100 mg, per day.

The derivative of the present invention, when administered together with a conjugated linoleic acid, can enhance the effect of reducing body fat according to the present invention. When the derivative of the present invention is used in combination with the conjugated linoleic acid, the mixing ratio between the derivative of the present invention and the conjugated linoleic acid may be properly regulated in the range of 0.01 to 100 parts by weight, preferably 0.1 to 40 parts by weight, of the conjugated linoleic acid, based on one part by weight of the derivative of the present invention.

When the derivative of the present invention or an extract composed mainly of this derivative is used as food or drink products or feeds (including pet foods), this may be used in the same form as the above pharmaceutical preparations, or alternatively may be in the form of solid or liquid foods or luxury foods, for example, agricultural foods, such as breads, noodles, boiled rice, confectionery (biscuits, cakes, candy or sweets, chocolates, Japanese-style confectionery), bean curds, and processed products thereof, fermented foods, such as refined sake, medicated wine, sweet sake, vinegar, soy sauce, and miso (fermented soybean paste), fat-and-oil foods, such as dressing, mayonnaise, margarin, shortenning, and edible fats and oils, livestock products, such as yoghurt, ham, bacon, and sousage, sea foods, such as boiled fish paste, fries of mixed ingredients, and fish cakes, and other processed products, such as fruit juice, refreshing drinks, sport drinks (isotonic drinks), alcoholic drinks, and teas.

When the derivative of the present invention or an extract composed mainly of this derivative is used as health foods or functional foods, this may be used in the form of pharmaceutical preparations or foods and drinks, or alternatively may be used, for example, in the form of processed forms, such as spontaneously fluidized foods, semi-digestion nutritional foods and ingredient nourishing foods with proteins (although lactoproteins, soybean proteins, egg albumin and other proteins, which have good amino acid balance and high nutritive value, are most widely used as a protein source, for example, degradation products thereof, oligopeptides of egg white, hydrolysates of soybean and the like and, in addition, a mixture of amino acids per se may also be used), saccharides, fat, trace elements, vitamins, emulsifiers, or spices being added thereto, and health drinks.

The food or drink product or feed according to the present invention may be produced by adding a predetermined amount of the derivative of the present invention or an extract composed mainly of the derivative to a food material substantially free from the derivative of the present invention and processing the mixture by a conventional method. The mixing ratio of the derivative or the extract may vary depending upon the dosage form and the form and properties of foods, and is not particularly limited. In general, however, the mixing ratio is preferably 0.001 to 50%.

Preferably, the amount of the food or drink product according to the present invention to be orally ingested is approximately such that the total amount of the derivative of the present invention is 1 mg to 10 g, preferably 1 mg to 2 g, more preferably 1 mg to 200 mg, per day per adult. Further, the food or drink product according to the present invention, when mixed with conjugated linoleic acid, can enhance the effect of reducing body fat attained by the derivative of the present invention. In this case, the mixing ratio between the derivative of the present invention and the conjugated linoleic acid may be in the range of 0.01 to 100 parts by weight, preferably 0.1 to 40 parts by weight, of the conjugated linoleic acid, based on one part by weight of the derivative of the present invention.

The following experimental examples demonstrate that dioxabicyclo[3.3.0]octane derivatives have activity to reduce body fat.

Conjugated linoleic acid and sesamin used in the following examples were prepared by the following method.

[Preparation of Conjugated Linoleic Acid (CLA)]

50 g of potassium hydroxide was dissolved in 150 g of propylene glycol. Nitrogen was then bubbled through the solution for 20 min, and the temperature was raised to 170° C. After raising the temperature, 100 g of a safflower oil was added to the solution, and a reaction was allowed to proceed at 170° C. for one hr under a nitrogen stream. After the completion of the reaction, the reaction solution was cooled to room temperature, and then neutralized with hydrochloric acid, followed by stirring for 15 min. Subsequently, the reaction solution was adjusted to pH 3, and distilled water was added thereto. The mixture was stirred for 5 min. Next, extraction with hexane was carried out three times. The hexane solution was washed with a 5% NaCl solution and distilled water, and then dehydrated and filtered. After the filtration, hexane was removed by distillation to give a conjugated linoleic acid-containing fatty acid.

[Preparation of Sesamin]

400 parts of an 80% aqueous ethanol solution as a solvent was added to 100 parts of scum as a by-product obtained in the production process of a sesame oil (a distillate obtained in the step of deodorization). The mixture was heated under reflux with stirring for one hr, cooled to 20° C., and then allowed to stand at that temperature overnight to prepare a mixed solution. The mixed solution consisted of two separated phases, a solvent-soluble fraction and a solvent-insoluble fraction. The solvent-soluble fraction was separated from the mixed solution by stratification separation. 24.7 parts of 48% potassium hydroxide was added to and mixed with the separated solvent-soluble fraction. The mixed solution was allowed to stand at 10° C. overnight to precipitate sesamins. The precipitated sesamins were separated by suction filtration, washed with 100 parts of water, and dried at 80° C. for 3 hr. Thus, a brown solid was obtained. The brown solid was analyzed and found to be a 1:1 mixture (purity 99.5%) of sesamin and episesamin.

EXAMPLE 1

Sprague-Dawley male rats of four weeks of age were acclimatized, and then divided into three groups (each group consisting of 8 rats), a 1.0% linoleic acid group (a control group), 0.2% sesamin group, and 0.2% sesamin+1.0% CLA group. The experimental diet shown in Table 1 and water were then freely fed to these three groups of rats. As shown in Table 2, the CLA used was composed mainly of two types, 9c,11t/9t,11c-18:2 and 10t,12c-18:2. Four weeks after the initiation of feeding, the 8 rats constituting each group were scarified, and the organs were taken out.

As a result, there was no significant difference in intake and weight gain between the groups.

Further, as shown in Table 3, there was no difference in the weight of tissues of liver, kidney, heart, lungs, spleen, and brain between the groups. On the other hand, for the sesamin-supplemented group, as compared with the control group, the weight of fat tissues around kidney and the weight of fat tissues around epididymis were reduced, and the reduction in these weights became more significant when the sesamin was used in combination with CLA.

As is apparent from the foregoing description, sesamin, either alone or in combination with CLA, has been proven to reduce fat tissues of rats without sacrificing the amount of feed ingested and weight gain, and thus can be used as an agent for reducing body fat.

TABLE 1

Composition of feed (AIN-93G)

| Ingredients | Experimental groups | | |
|---|---|---|---|
| | Control group | Sesamin group | Sesamin + CLA group |
| | (g/100 g) | | |
| Casein | 20.0 | 20.0 | 20.0 |
| Soybean oil | 6.0 | 6.0 | 6.0 |
| α-Cornstarch | 13.2 | 13.2 | 13.2 |
| Sucrose | 10.0 | 10.0 | 10.0 |
| Mineral mix (AIN-93G) | 3.5 | 3.5 | 3.5 |
| Vitamin mix (AIN-93VX) | 1.0 | 1.0 | 1.0 |
| L-Cystine | 0.3 | 0.3 | 0.3 |
| Choline tartrate | 0.25 | 0.25 | 0.25 |
| Cellulose | 5.0 | 5.0 | 5.0 |
| t-Butylhydroquinone | 0.0014 | 0.0014 | 0.0014 |
| Cornstarch | 39.7 | 39.5 | 39.5 |
| LA (safflower oil) | 1.0 | 1.0 | — |
| Sesamin | — | 0.2 | 0.2 |
| CLA | — | — | 1.0 |

TABLE 2

CLA and fatty acid composition of safflower oil

| | CLA | Safflower oil |
|---|---|---|
| C16: 0 (palmitic acid) | 6.9 | 6.7 |
| C18: 0 (stearic acid) | 2.4 | 2.4 |
| C18: 1 (oleic acid) | 15.3 | 15.1 |
| C18: 2 (linoleic acid) | 0.7 | 74.1 |
| CLA (conjugated linoleic acid) | 74.1 | n.d. |
| c9, t11/t9, c11–18:2 | (34.1) | — |
| t10, c12–18:2 | (35.9) | — |
| c9, c11/c10, c12–18:2 | (2.5) | — |
| t9, t11/t10, t12–18:2 | (1.6) | — |
| C18: 3 (α-linolenic acid) | — | 0.5 |
| Others | 0.6 | 1.2 |

TABLE 3

Growth and weight of organs of rats

| Parameter | Experimental groups | | |
|---|---|---|---|
| | Control group | Sesamin group | Sesamin + CLA group |
| Weight gain, g/4 weeks | 217 | 222 | 219 |
| Intake of feed, g/day | 21.0 | 20.8 | 20.5 |
| Weight of organs, g/100 g body weight | | | |
| Liver | 4.36 | 4.88 | 5.15 |
| Kidney | 0.75 | 0.76 | 0.77 |
| Heart | 0.39 | 0.35 | 0.36 |
| Lung | 0.42 | 0.39 | 0.39 |
| Spleen | 0.22 | 0.23 | 0.21 |
| Brain | 0.40 | 0.40 | 0.39 |
| Peri-renal adipose tissue | 1.72 | 1.47 | 0.97 |
| Epididymal adipose tissue | 1.13 | 1.02 | 1.00 |

EXAMPLE 2

Sprague-Dawley male rats of four weeks of age were acclimatized for 5 to 11 days, and then divided into three groups (each group consisting of 5 rats), a 1.0% linoleic acid group (a control group), 0.2% sesamin group, and 0.2% sesamin+1.0% CLA group. In the experiment, CE-2 (lipid content 4.5%) manufactured by CLEA JAPAN INC. with 1.5% of a soybean oil being added thereto was used as a basic diet, and the experimental diet was freely fed to the rats. As shown in Table 2, the CLA used was composed mainly of two types, 9c,11t/9t,11c-18:2 and 10t,12c-18:2. Three weeks after the initiation of feeding, a liver perfusion experiment was carried out.

As a result, as shown in Table 4, there was no difference in intake and weight gain between the groups.

Further, as shown in Table 5, it was confirmed that, for the sesamin-supplemented group, as compared with the control group, the amount of triglyceride secreted from the perfused liver was reduced, and the reduction in the amount of secretion became more significant when the sesamin was used in combination with CLA.

As is apparent from the foregoing description, sesamin, either alone or in combination with CLA, is considered to reduce the amount of triglyceride secreted from the liver without sacrificing food intake and weight gain of rats, leading to a reduction in body fat.

TABLE 4

Food intake and weight gain of rats

| | Experimental groups | | |
|---|---|---|---|
| | Control group | Sesamin group | Sesamin + CLA group |
| Food intake, g/day | 25.9 | 25.3 | 25.0 |
| Weight gain, g/day | 8.64 | 8.22 | 8.26 |

TABLE 5

Amount of triglyceride secreted from perfused liver

| | Experimental groups | | |
|---|---|---|---|
| | Control group | Sesamin group | Sesamin + CLA group |
| | μmol/liver | | |
| 1 hr after initiation of perfusion | 4.77 | 3.19 | 2.69 |
| 2 hr after initiation of perfusion | 14.1 | 8.94 | 7.52 |
| 3 hr after initiation of perfusion | 25.1 | 16.8 | 13.8 |
| 4 hr after initiation of perfusion | 36.0 | 25.3 | 20.4 |

What is claimed is:

1. A method for reducing body fat in an animal, comprising administering to said animal a dioxabicyclo[3.3.0]octane derivative represented by formula (I):

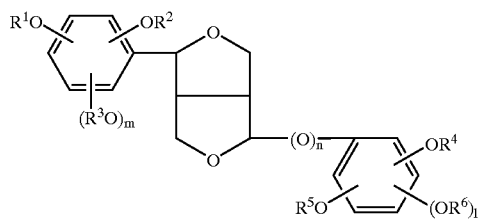

wherein $R^1$ to $R^6$ each independently represent a hydrogen atom or an alkyl group having 1 to 3 carbon atoms, provided that $R^1$ and $R^2$ and/or $R^4$ and $R^5$ combine together to form a methylene or ethylene group; and n, m, and l are each 0 or 1.

2. The method of claim 1, wherein said dioxabicyclo[3.3.0]octane derivative is selected from the group consisting of sesamine, sesaminol, episesamine, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]-octane, 2-(3,4-methylenedioxyphenyl)-6-(3-methoxy-4-hydroxyphenoxy)-3,7-dioxabicyclo[3.3.0]octane, and mixtures thereof.

3. The method of claim 1, wherein said dioxabicyclo[3.3.0]octane derivative is in the form of a food or drink or an animal feed composition.

4. The method of claim 3, wherein said food or drink or animal feed composition is a pet food.

5. The method of claim 1, wherein said dioxabicyclo[3.3.0]octane derivative is in the form of a pharmaceutical composition.

* * * * *